United States Patent [19]

Delzell, Sr.

[11] 4,172,888

[45] Oct. 30, 1979

[54] ATHLETE'S FOOT TREATMENT

[75] Inventor: Robert E. Delzell, Sr., Rte. 4, Lakeview Dr., Lenoir City, Tenn. 37771

[73] Assignee: Robert E. Delzell, Sr., Lenoir City, Tenn.

[21] Appl. No.: 941,380

[22] Filed: Sep. 12, 1978

[51] Int. Cl.$^2$ .................... A61K 33/02; A61K 31/20; A61K 31/12

[52] U.S. Cl. ................................ 424/166; 424/318; 424/331

[58] Field of Search .................... 424/318, 166, 331

[56] References Cited

U.S. PATENT DOCUMENTS

| 155,820 | 10/1874 | Anderson | 424/166 |
|---|---|---|---|
| 1,455,052 | 4/1934 | Durwell | 424/318 X |
| 1,901,434 | 3/1933 | Cade et al. | 424/318 X |
| 2,021,131 | 11/1935 | McDaniel | 424/318 X |
| 2,100,469 | 11/1937 | Burwell | 424/318 |
| 2,299,604 | 10/1942 | Weirich | 424/166 X |
| 3,395,236 | 7/1968 | White | 424/318 X |

OTHER PUBLICATIONS

Chemical Abstracts 55:18876b (1961).
Chemical Abstracts 55:23933g (1961).
Chemical Abstracts 65:2663h (1966).
Chemical Abstracts 47:10931a (1953).
Gregory—Uses & Applications of Chemicals & Related Materials, pp. 5 & 6, (1939).

*Primary Examiner*—Leonard Schenkman
*Attorney, Agent, or Firm*—Pitts & Kesterson

[57] ABSTRACT

The use of a solution of oleic acid, acetone, ammonium hydroxide and water as a treatment of athlete's foot and ringworm. The treatment comprises a topical application of the solution or for cases of acute athlete's foot, soaking the affected members in a diluted solution. The solution comprises about 4 parts oleic acid mixed with acetone. The oleic acid and acetone mixture is then mixed with 8 parts of aqua ammonia (ammonium hydroxide) to form a concentrated solution. This concentrated solution is then diluted with 128 parts of water for soaking applications and 32 parts water for topical applications.

6 Claims, No Drawings

ATHLETE'S FOOT TREATMENT

BACKGROUND OF THE INVENTION

This invention relates to a composition having germicidal and fungicidal properties, and more particularly to a composition for treating fungicidal infections such as ringworm and athlete's foot. The composition is also effective as a germicide for treating cuts and scratches to avoid infection and fungus infestations.

An investigation revealed the following U.S. Patents that were related to the present invention. U.S. Pat. No. 1,901,434 issued to Cade et al discloses a composition having germicidal and detergent properties. This patent disclosed that when a soap of an unsaturated fatty acid (including, for example, sodium oleate) which by itself is not highly germicidal, and an alkaline substance having a Ph range of 7 to 14 (including for example, sodium phosphate and sodium hydroxide) which by itself is not highly germicidal are combined, the composition becomes highly germicidal. It will be appreciated, however, that the composition of this patent does not include the unique ingredients of the present invention, nor is there any teaching or claim to the composition having fungicidal properties.

U.S. Pat. No. 2,021,131 issued to McDaniel discloses a composition which provides protection of organic tissues against injurious elements such as acid fumes, printers ink, gasoline, naptha distillates, grease, oils, paint, etc. The patent discloses a method of producing the composition as well as the makeup of the composition which includes water, a saponaceous material such as sodium stearate, sodium silicate and a polyhydroxyl alcohol such as glycerin. This patent discloses a well known coating and protective composition. However, it in no way even suggests a composition having germicidal or fungicidal properties much less a composition comprised of the ingredients of the present invention which has fungicidal and germicidal properties.

U.S. Pat. No. 2,100,469 issued to C. Burwell discloses a composition having germicidal and fungicidal properties as well as a method of preparation. The composition is a saponifiable composition comprising synthetic fatty acids derived from an oxidized petroleum hydrocarbon and an akaline metal hydroxide. However, it will be appreciated by those skilled in the art that the fatty acid, oleic acid is not normally obtained from petroleum hydrocarbon, but instead is obtained from vegetable oils and animal fats. In addition, although ammonia hydroxide (aqua ammonia) is an alkali, it is not a metal alkali. Furthermore, there is, of course, no teaching of acetone as an ingredient in this prior art patent.

U.S. Pat. No. 3,395,236 discloses a unctuous composition for carrying fungicides and therapeutic ingredients deep into tissue including as examples, fingernails and toenails where fungi and other disease organisms have penetrated. The composition includes unsaturated fatty acids such as oleic and linoleic acids, a polyhydric alcohol such as polyethlene glycol, a nitrogen source such as gelatin, a natural amino acid and a surface active agent such as lauryl sulfate. This composition provides a penetrating agent, which may be mixed with a fungicide to carry the fungicide deep into tissue. However, there is no claim or teaching that the composition itself is fungicidal or germicidal. In addition, it will be appreciated that none of the components of this composition other than the oleic acid are in any way similar to the components of the present invention. Furthermore, these ingredients such as polyhydric alcohol, gelatin, a natural amino acid are in no way suggestive of the components of the present invention.

Other commercially available and effective fungicides include undecylenic acid and a metallic salt. For example, certain fungicides, include undecylenic acid in combination with the zinc salt of undecylenic acid whereas other commercial fungicides includes undecylenic acid in combination with the potassium salt of undecylenic acid. It might be considered by some that undecylenic acid could suggest oleic acid which has a similar structure. However, in no way does a metallic salt suggest the use of an ammonia salt. Furthermore, the use of acetone is in no way suggested by any of the fungicides available.

Therefore, although the compositions discussed above do demonstrate fungicidal properties and include some of the same ingredients as the present invention, none of the patents disclose all of the ingredients of the present invention nor do they when considered separately or in combination even suggest much less teach the unusual combination of ingredients as the present invention.

It may also be considered of importance that a composition substantially similar to that described in the present invention has been used in the past as a degreasing and cleansing agent for small machinery such as watches and clocks. However, nowhere is there any suggestion much less a teaching of the novel and new use of the composition of this invention as a fungicide for use in treating ringworm and athlete's foot.

SUMMARY OF THE INVENTION

Therefore, it is an object of this invention to provide a simple and inexpensive fungicidal composition particularly applicable for the treatment of ringworm and athlete's foot.

It is another object of this invention to provide a germicidal composition for treating cuts and scratches to avoid infections.

With this and other objects in view, briefly, the invention comprises a mixture of an unsaturated fatty acid which commonly serves as a soap base such as oleic acid, acetone, ammonium hydroxide and water.

DESCRIPTION OF THE INVENTION

According to this invention, it has been found that a composition comprising a solution of the unsaturated fatty acid oleic acid, the ketone acetone, commercially available 52% aqua ammonia (ammonium hydroxide) and water has pronounced utility as an effective fungicide and especially as a cure for ringworm and athlete's foot. The solution also acts as a germicide and has been found effective for treating cuts and scratches to prevent infection. The method of applying the solution to obtain the germicidal and fungicidal effects, is not critical, as it is equally effective when sprayed or applied to the affected site by an applicator such as cotton. In addition, a diluted solution used as a bath for soaking the feet or affected parts has been found to be especially effective in treating acute cases of athlete's foot. The composition is prepared by mixing the oleic acid and the acetone. The aqua ammonia (ammonium hydroxide) is then slowly and thoroughly stirred into the oleic acid and acetone mixture. As will become clear in the working examples discussed hereinafter, ammonium hydroxide in excess of that required to fully combine with the oleic acid is used. Oleic acid ($C_{17}H_{33}COOH$) has a molecular weight of 282. Therefore, since the molecular weight of pure aqua ammonia or ammonium hydroxide ($NH_4OH$) is 35 it will be appreciated by those skilled in the art that oleic acid will fully combine with ammonium hydroxide to form ammonium oleate at a ratio of around 8 parts oleic acid to 1 part ammonium hydroxide. However, as will be seen in the working examples described hereinafter, the composition uses ammonium hydroxide greatly in excess of that necessary for fully combining with the oleic acid. This composition with the excessive ammonium hydroxide has resulted in a surprisingly fast and effective cure of athlete's foot. Therefore, it is believed to be important that the ratio of oleic acid to ammonium hydroxide not be greater than 8:1 (or 1:1/8). However, because of the strong and disagreeable odor of ammonium hydroxide and to avoid diluting the ammonium oleate resulting from the combining of oleic acid and ammonium hydroxide as well as the acetone, it is suggested that the ratio of oleic acid to ammonium hydroxide should not be less that 1:2 as substantially shown in the working examples. The amount of acetone used is not believed to be critical since as will be appreciated by those skilled in the art, there will be no chemical reaction between this volatile solvent and the other ingredients. However, to be assured of the excellent fungicidal properties of this composition, it is suggested that enough acetone be included such that the composition maintains the properties of a mild solvent. On the other hand, acetone should not be used in proportions large enough to cause damage to the skin or other tissue. To this end, it is believed that the amount of acetone used in the composition should be between about 1 part acetone to 2 parts oleic acid (or ½ part acetone to 1 part oleic acid) and 3 parts acetone to 1 part oleic acid, and preferably 3 parts acetone to 2 parts oleic acid. Thus, it is believed that combinations of oleic acid, acetone and ammonium hydroxide within the ranges described above should result in the composition having the beneficial fungicidal and germicidal properties of this invention. Furthermore, it is also believed that the amount of water used in the mixture and composition is not critical, but should be sufficient to achieve the desired viscosity of the mixture and to dilute the mixture depending upon whether the composition is to be a topical application such as by spray or swab, or whether it is to be used as a soaking bath such as a foot bath. To this end, it has been found that for a concentrated solution suitable for directly applying to the affected site, a solution of about 2 parts water to 1 part of the mixture of oleic acid, acetone and ammonium hydroxide should be used. For a diluted solution suitable for a foot bath, a solution of about 8 parts water to 1 part of the composition of oleic acid, acetone and ammonium hydroxide should be used.

By way of illustration, two embodiments of the invention are presented in the following working examples. However, it is to be understood that although the invention will be further clarified by a consideration of the following examples, such examples are intended to be purely exemplary of the use of this invention and are not to be construed as limiting the scope of this invention except as may be set out in the claims.

EXAMPLE I

According to the first embodiment of this invention, 4 oz (4 parts) of oleic acid were carefully and thoroughly mixed with 6 oz (6 parts) of acetone. This oleic acid and acetone mixture was then slowly stirred into 8 oz (8 parts) of 52% commercial aqua ammonia or ammonium hydroxide. The mixture of oleic acid, acetone and ammonium hydroxide was then mixed with 1 gallon (128 parts) of water to obtain a diluted solution. Such a solution has been used as a soaking bath in a very fast an effective treatment of acute athlete's foot which was unresponsive to other available treatments.

EXAMPLE II

A concentrated form of the present composition suitable for use for direct application to sites affected with ringworm or athlete's foot is obtained by preparing the composition in the same manner as discussed in Example I above except that the mixture uses 1 quart (32 parts) of water rather than 1 gallon of water. A topical application of this concentrated composition should result in effective treatment of athlete's foot and ringworm.

Although the present invention has been discussed with respect to the specific examples, it is not intended that such specific examples be limitations upon the scope of the invention except as insofar as is set forth in the following claims.

What is claimed is:

1. A method of providing a germicidal and fungicidal treatment of live animal tissue which comprises applying to the affected tissue a solution comprising water and a mixture of acetone, oleic acid and ammonium hydroxide; said mixture having a ratio between oleic acid and ammonium hydroxide which ranges between 1 part oleic acid to ⅛ part ammonium hydroxide and 1 part oleic acid to 2 parts ammonium hydroxide, and a ratio between oleic acid to acetone which ranges between 1 part oleic acid to ½ part acetone and 1 part oleic acid to 3 parts acetone; said solution having a ratio between said mixture and water which ranges between 1 part mixture to 32 parts water and 1 part mixture to 128 parts water.

2. The method of claim 1 wherein said mixture of acetone, oleic acid and ammonium hydroxide is obtained by mixing 4 parts oleic acid with 6 parts of acetone, and then adding and mixing 8 parts of 52% ammonium hydroxide, and wherein said mixture of oleic acid, acetone and ammonium hydroxide is then diluted with water.

3. The method of claim 2 or 1 wherein said mixture of oleic acid, acetone and ammonium hydroxide is diluted with 32 parts water.

4. The method of claim 2 or 1 wherein said mixture of oleic acid, acetone and ammonium hydroxide is diluted with 128 parts water.

5. The method of claim 2 or 1 wherein the provided treatment is a fungicidal treatment for curing ringworm and athlete's foot.

6. The method of claim 2 or 1 wherein the provided treatment is a germicidal treatment for cuts and scratches.

* * * * *